(12) United States Patent
Hong et al.

(10) Patent No.: US 11,465,959 B2
(45) Date of Patent: Oct. 11, 2022

(54) METHOD FOR PREPARING 4,4'-DIHYDROXY-[1,1'-BIPHENYL-3,3'-DICARBOXYLIC ACID]

(71) Applicant: Korea University Research and Business Foundation, Seoul (KR)

(72) Inventors: Chang Seop Hong, Seoul (KR); Jong Hyeak Choe, Seoul (KR); Jeong Eun Kim, Incheon (KR)

(73) Assignee: Korea University Research and Business Foundation, Seoul (KR)

( * ) Notice: Subject to any disclaimer, the term of this patent is extended or adjusted under 35 U.S.C. 154(b) by 38 days.

(21) Appl. No.: 17/050,925

(22) PCT Filed: Apr. 30, 2019

(86) PCT No.: PCT/KR2019/005212
§ 371 (c)(1),
(2) Date: Oct. 27, 2020

(87) PCT Pub. No.: WO2019/212233
PCT Pub. Date: Nov. 7, 2019

(65) Prior Publication Data
US 2021/0230092 A1    Jul. 29, 2021

(30) Foreign Application Priority Data

Apr. 30, 2018  (KR) .................. 10-2018-0049962
Apr. 29, 2019  (KR) .................. 10-2019-0049887

(51) Int. Cl.
*C07C 51/15*   (2006.01)
*C07C 51/50*   (2006.01)
*C07C 65/105*  (2006.01)

(52) U.S. Cl.
CPC .............. *C07C 51/15* (2013.01); *C07C 51/50* (2013.01); *C07C 65/105* (2013.01)

(58) Field of Classification Search
CPC ........................... C07C 51/15; C07C 65/105
USPC ........................................................ 562/492
See application file for complete search history.

(56) References Cited

U.S. PATENT DOCUMENTS

2005/0228195 A1* 10/2005 Wytcherley ........... C07C 51/487
562/486
2013/0053585 A1   2/2013 Long et al.

FOREIGN PATENT DOCUMENTS

| JP | 2015-504000 A | 2/2015 |
| KR | 10-2007-0018942 A | 2/2007 |
| KR | 10-2017-0043921 A | 4/2017 |
| WO | 2009/011545 A2 | 1/2009 |

OTHER PUBLICATIONS

Maserati et al Chemistry of Materials (2016), 28(5), 1581-1588.*
Giani et al. Computers and Chemical Engineering 29 (2005) 1661-1676.*
Zheng-Ping Wu, et al., "Framework-solvent interactional mechanism and effect of NMP/DMF on solvothermal synthesis of [$Zn_4O(BDC)_3$]$_8$", Transactions of Nonferrous Metals Society of China, 2014, pp. 3722-3731, vol. 24.
International Search Report for PCT/KR2019/005212 dated Aug. 23, 2019 [PCT/ISA/210].

* cited by examiner

*Primary Examiner* — Ana Z Muresan
(74) *Attorney, Agent, or Firm* — Sughrue Mion, PLLC

(57) ABSTRACT

The present invention relates to a method for preparing 4,4'-dihydroxy-[1,1'-biphenyl-3,3'-dicarboxylic acid], the method comprising a step for preparing a compound represented by chemical formula 1 by reacting a compound represented by chemical formula 2 with a base according to reaction formula 1. [reaction formula 1] [chemical formula 1] [chemical formula 2] According to the present invention, because use of additional carbon dioxide is unnecessary during the reaction, internal pressure is lowered during same, the reaction can be carried out at a lower temperature, the yield from the synthesis is notably improved as hardening of the resulting substance is absent, and $H_4$dobpdc can be synthesized in large amounts as an additional process for obtaining pure ligands is unnecessary.

6 Claims, 8 Drawing Sheets

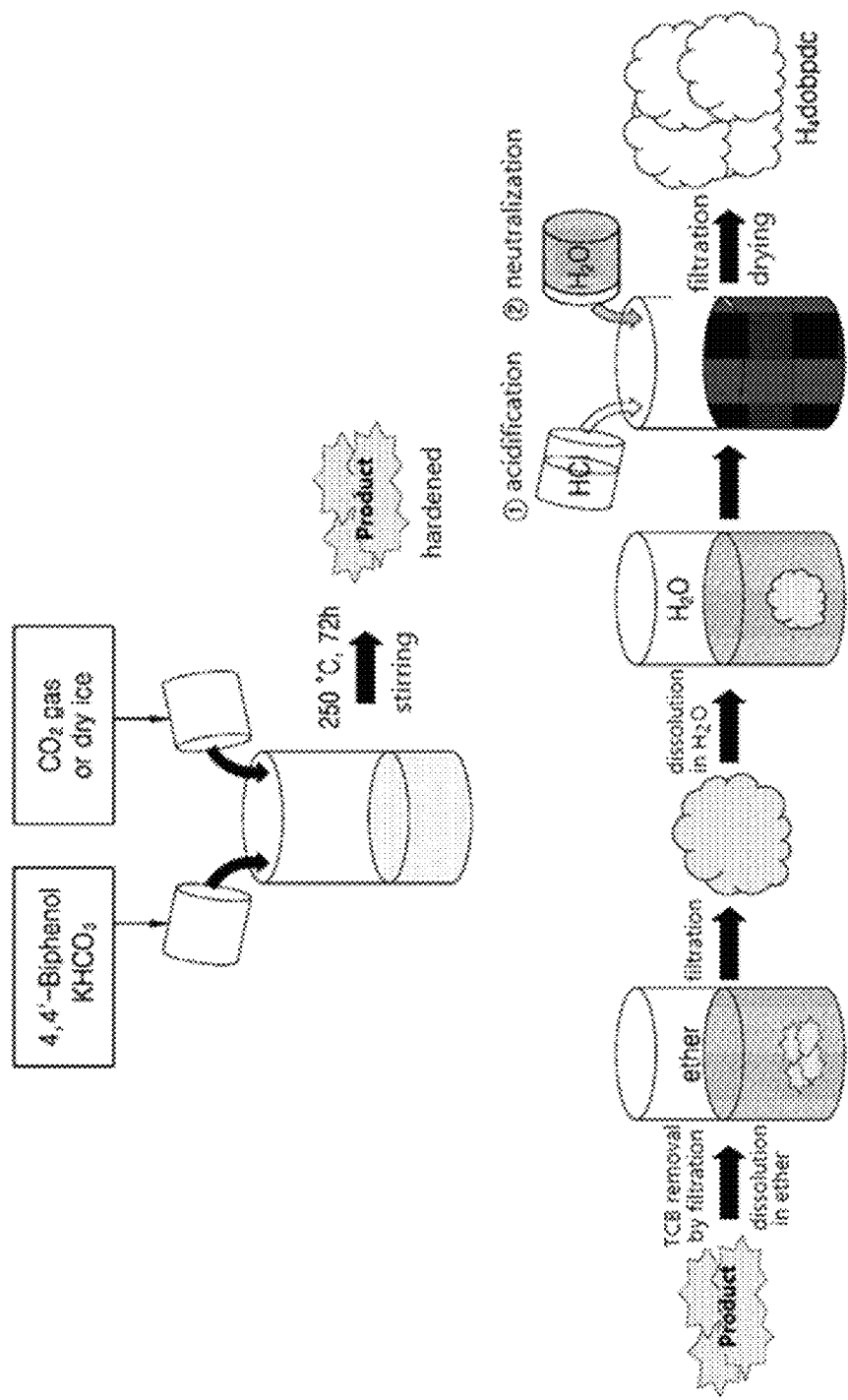
[Fig. 1]

[Fig. 2]
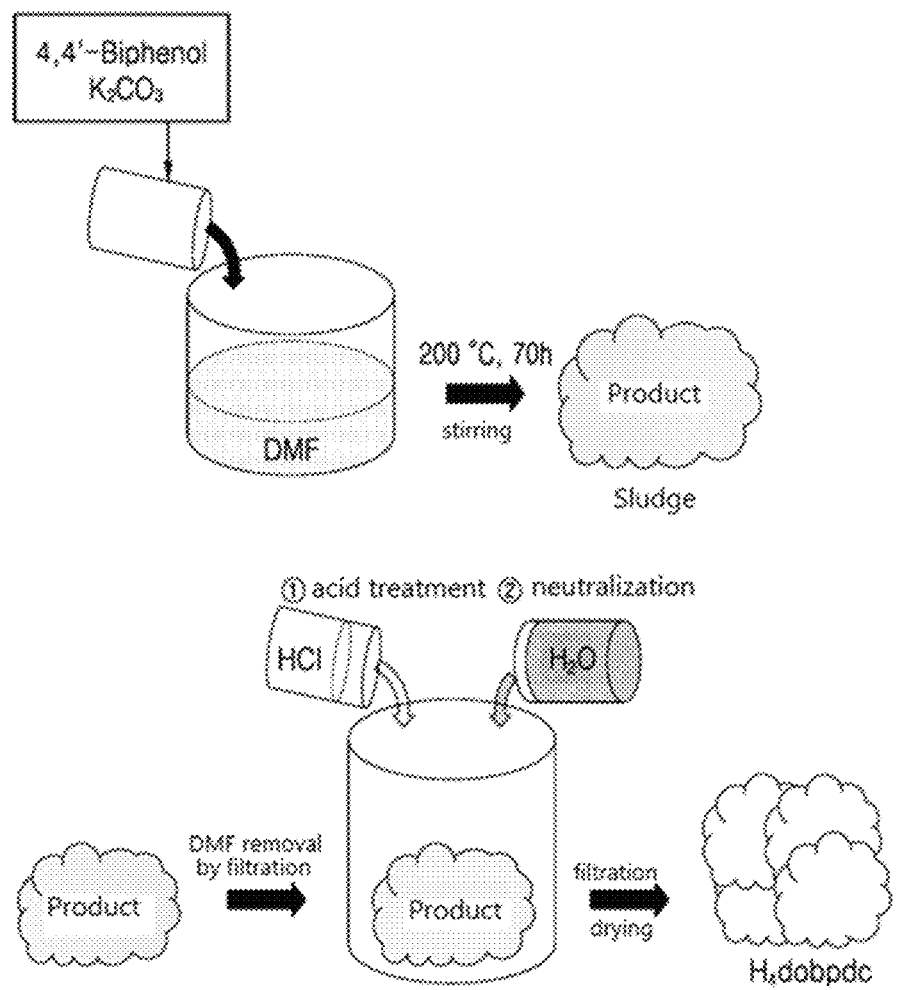

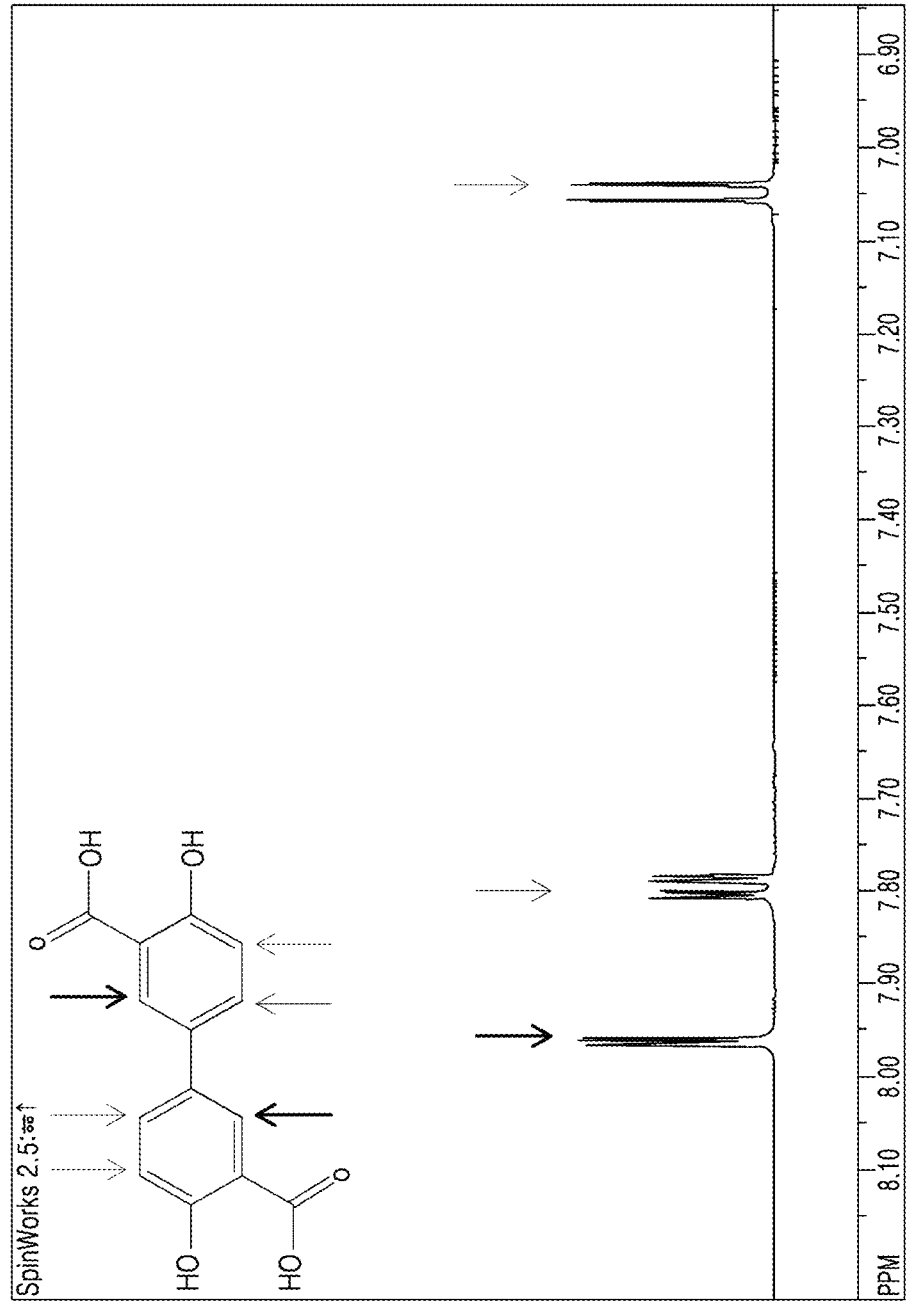
[Fig. 3]

[Fig. 4]
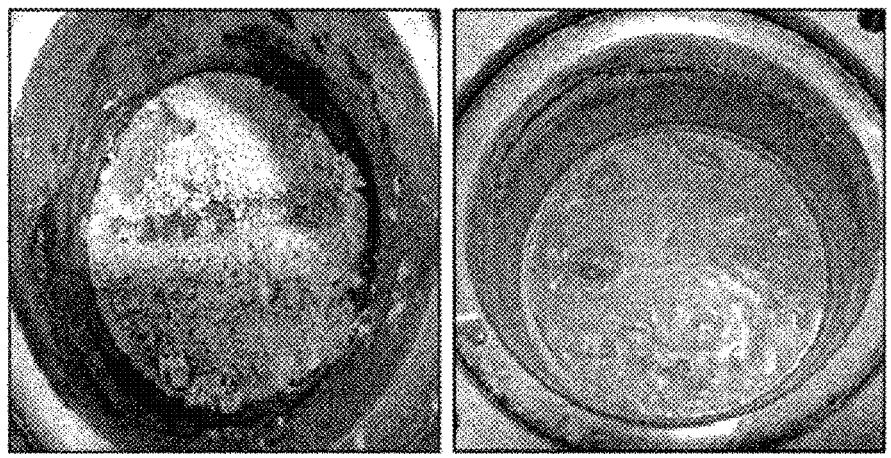

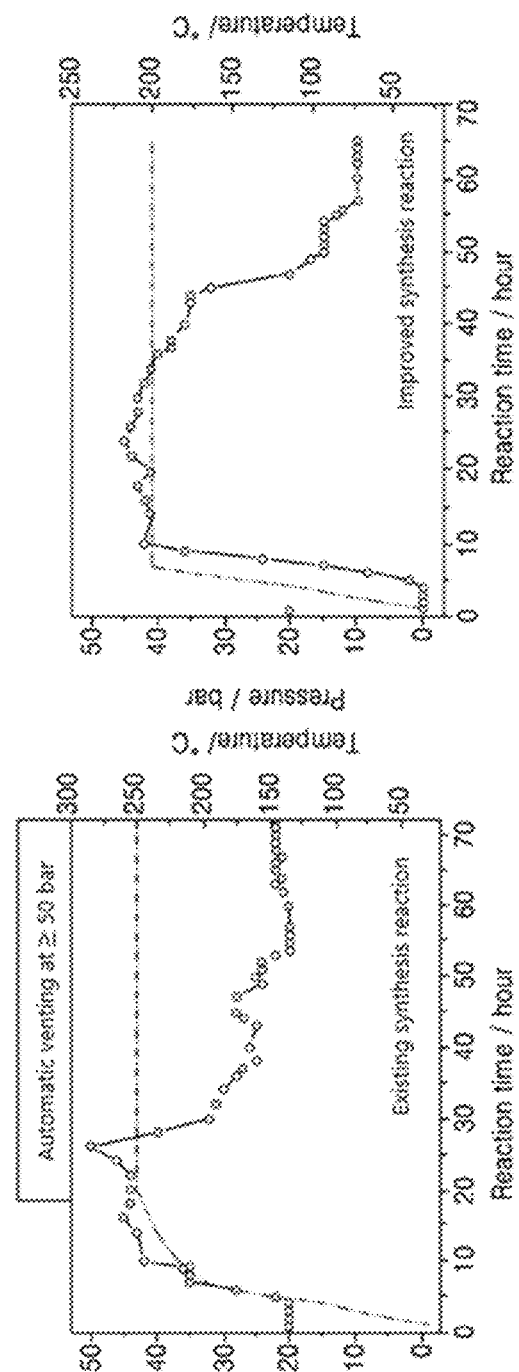
[Fig. 5]

[Fig. 6]
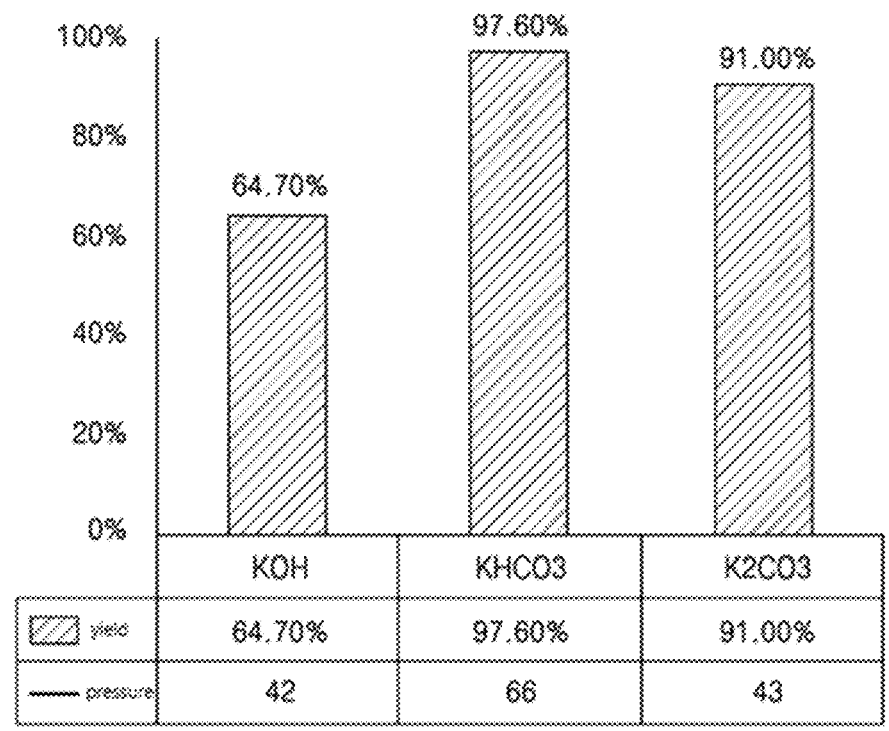
[Fig. 7]
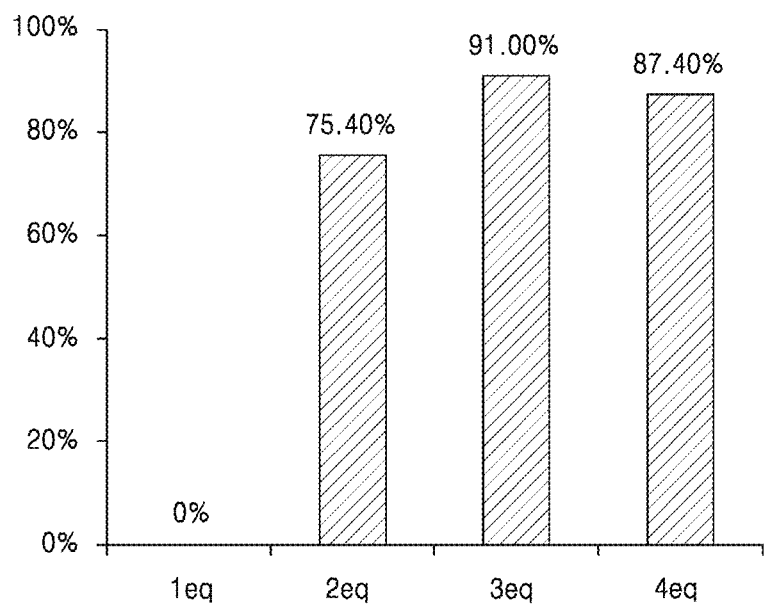

[Fig. 8]
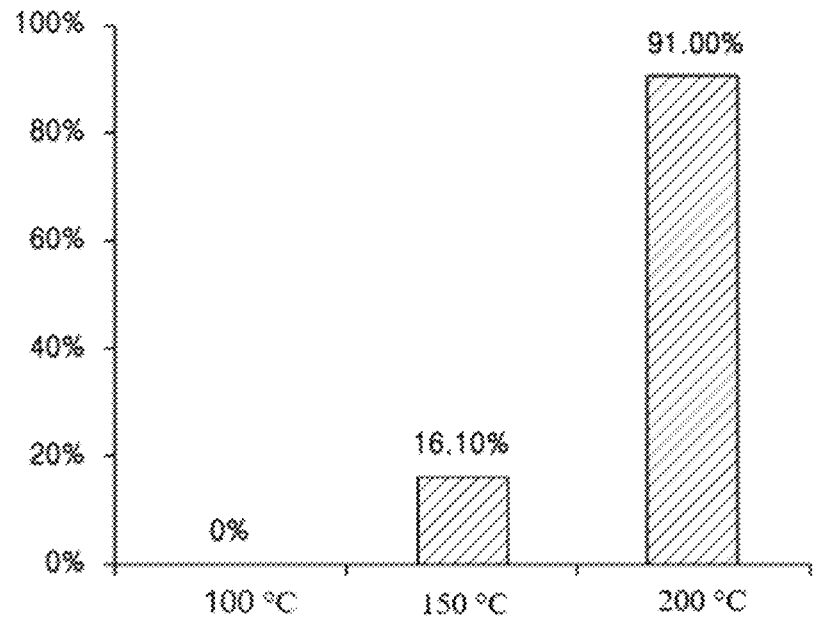
[Fig. 9]
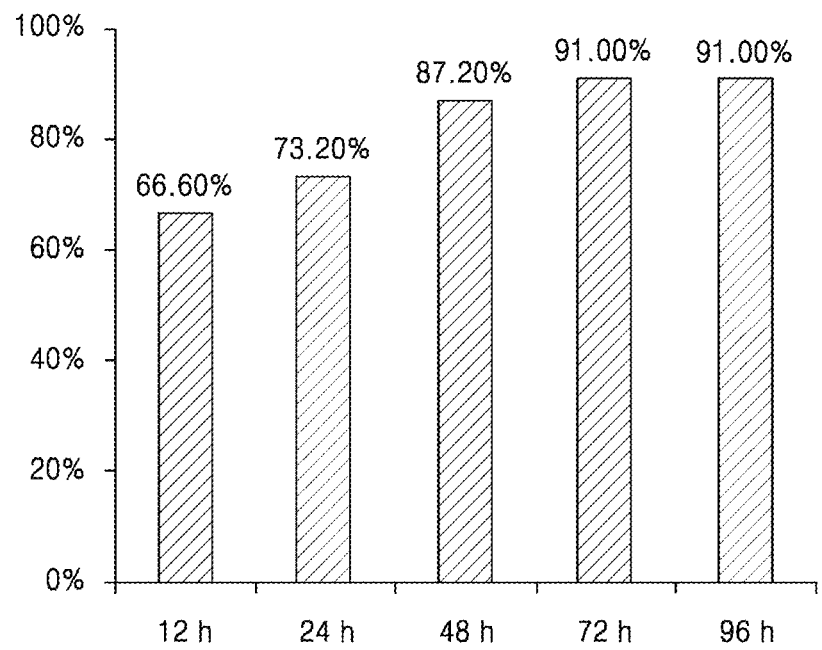

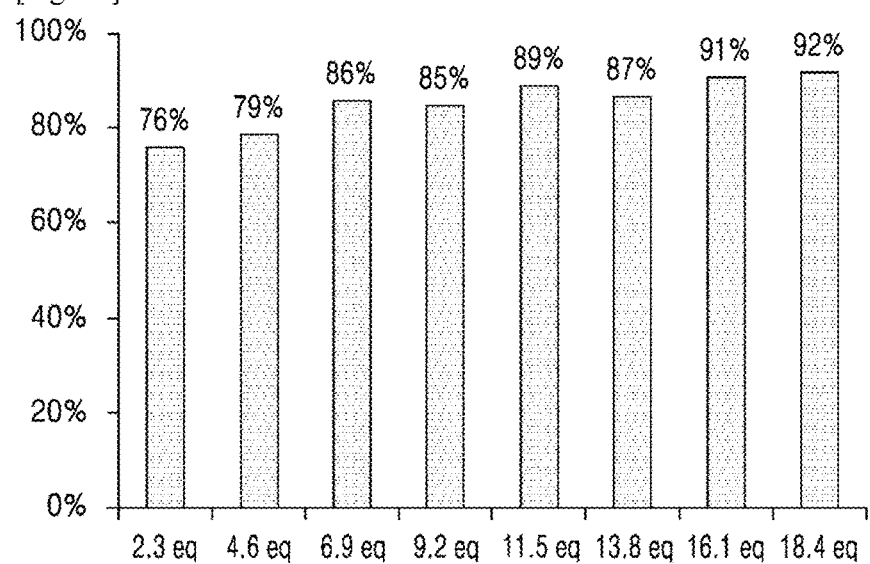
[Fig. 10]

METHOD FOR PREPARING 4,4'-DIHYDROXY-[1,1'-BIPHENYL-3,3'-DICARBOXYLIC ACID]

TECHNICAL FIELD

The present invention relates to a method for preparing 4,4'-dihydroxy-[1,1'-biphenyl-3,3'-dicarboxylic acid].

BACKGROUND ART

Since the Industrial Revolution, global warming caused by increased carbon dioxide in flue gases from thermal power stations has emerged as a global environmental issue. Under such circumstances, an increasing interest has focused on the development of adsorbents capable of selectively adsorbing carbon dioxide. Particularly, diamine-$M_2$(dobpdc), a metal-organic framework (MOF) functionalized with diamine, is known to be very effective in capturing carbon dioxide and its mass production is thus required for capturing carbon dioxide whose levels are rising rapidly. For the mass production of $M_2$(dobpdc), it is necessary to produce 4,4'-dihydroxy-[1,1'-biphenyl-3,3'-dicarboxylic acid] (hereinafter referred to as "$H_4$dobpdc") on a large scale. $H_4$dobpdc is an organic framework of $M_2$(dobpdc).

In this connection, a method for synthesizing $H_4$dobpdc by reacting 4,4'-biphenol ([1,1'-biphenyl]-4,4'-diol) with $KHCO_3$ as a base in trichlorobenzene (TCB) as a solvent was reported in the literature (see Non-Patent Document 1 and FIG. 1). However, this method is not suitable for the mass production of $H_4$dobpdc due to the following disadvantages. First, the product is hardened during the reaction in a large-scale (≥300 mL) reactor. Since this phenomenon impedes stirring during the reaction, the reaction does not proceed perfectly, resulting in a very low yield of the product. Further, an additional supply of carbon dioxide gas is needed during the reaction, leading to an increase in internal pressure. A high temperature is also necessary for the reaction, causing poor reaction stability. Moreover, a complex separation process is required to obtain the ligand in a pure form.

There is thus a need to develop a novel method for synthesizing $H_4$dobpdc on a large scale while avoiding the above-described problems.

(Non-Patent Document 1) McDonald, T. M.; Lee, W. R.; Mason, J. A.; Weirs, B. M.; Hong, C. S.; Long, J. R. "Capture of Carbon Dioxide from Air and Flue Gas in the Alkylamine-Appended Metal-Organic Framework mmen-$Mg_2$(dobpdc)", *J. Am. Chem. Soc.* 2012, 134, 7056)

DETAILED DESCRIPTION OF THE INVENTION

Problems to be Solved by the Invention

The present invention has been made in an effort to solve the above-described problems and intends to provide a novel method for synthesizing $H_4$dobpdc on a large scale.

Means for Solving the Problems

One aspect of the present invention provides a method for preparing 4,4'-dihydroxy-[1,1'-biphenyl-3,3'-dicarboxylic acid] represented by Formula 1, including reacting the compound represented by Formula 2 with a base, as depicted in Reaction 1:

[Reaction 1]

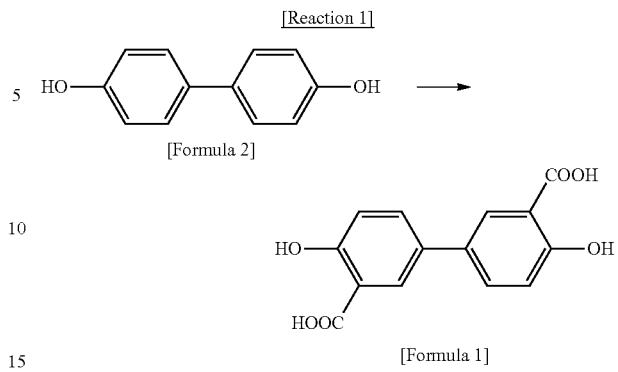

[Formula 2]

[Formula 1]

Reaction 1 is carried out in a solvent represented by Formula 3:

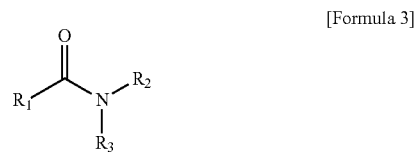

[Formula 3]

wherein $R_1$ is H or $-(CH_2)_n-CH_3$, $R_2$ is $-(CH_2)_m-CH_3$, $R_3$ is $-(CH_2)_p-CH_3$, and n, m, and p are each independently an integer from 0 to 20.

According to the present invention, the base may be selected from the group consisting of $K_2CO_3$, $Na_2CO_3$, $Li_2CO_3$, $KHCO_3$, $NaHCO_3$, $LiHCO_3$, and KOH.

According to the present invention, the solvent represented by Formula 3 may be selected from the group consisting of the compounds represented by Formulae 4 to 7:

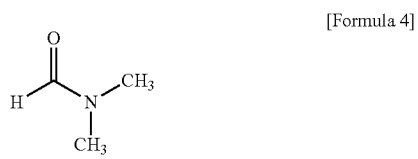

[Formula 4]

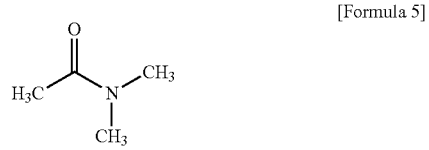

[Formula 5]

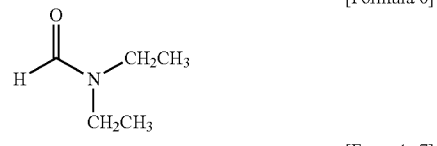

[Formula 6]

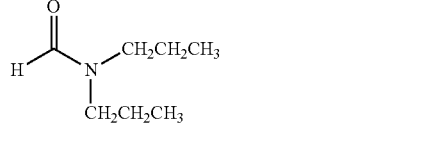

[Formula 7]

According to the present invention, the base may be used in an amount of 2 to 4 equivalents per equivalent of the compound represented by Formula 2.

According to the present invention, the solvent represented by Formula 3 may be used in an amount of 1 to 30 equivalents per equivalent of the compound represented by Formula 2.

According to the present invention, Reaction 1 may be carried out at a temperature of 170 to 230° C.

According to the present invention, Reaction 1 may be carried out for at least 12 hours.

Effects of the Invention

Since the present invention avoids the need to further use carbon dioxide during the reaction, the internal pressure is lowered during the reaction and the reaction is allowed to proceed at a lower temperature. In addition, the product is prevented from becoming hard, resulting in a significant increase in yield. Furthermore, no additional process is required to obtain the ligand in a pure form. Therefore, the present invention enables the synthesis of $H_4$dobpdc on a large scale.

BRIEF DESCRIPTION OF THE DRAWINGS

FIG. 1 schematically shows a process for preparing and separating $H_4$dobpdc according to the prior art.

FIG. 2 schematically shows a process for preparing and separating $H_4$dobpdc according to the present invention.

FIG. 3 is a nuclear magnetic resonance (NMR) spectrum of $H_4$dobpdc prepared in Example 1.

FIG. 4 shows images of a ligand prepared by a method for synthesizing $H_4$dobpdc according to the prior art and a ligand prepared by a method for synthesizing $H_4$dobpdc according to the present invention.

FIG. 5 shows the temperature-pressure relationships of a reactor used for a reaction in a method for synthesizing $H_4$dobpdc according to the prior art and a reactor used for a reaction in a method for synthesizing $H_4$dobpdc according to the present invention.

FIG. 6 shows the yields of $H_4$dobpdc synthesized using different types of bases according to the present invention.

FIG. 7 shows the yields of $H_4$dobpdc synthesized using different equivalent amounts of a base according to the present invention.

FIG. 8 shows the yields of $H_4$dobpdc synthesized at different reaction temperatures according to the present invention.

FIG. 9 shows the yields of $H_4$dobpdc synthesized for different reaction times according to the present invention.

FIG. 10 shows the yields of $H_4$dobpdc synthesized using different equivalent amounts of a solvent according to the present invention.

BEST MODE FOR CARRYING OUT THE INVENTION

Unless otherwise defined, all technical and scientific terms used herein have the same meaning as commonly understood by one of ordinary skill in the art to which this invention belongs. In general, the nomenclature used herein is well known and commonly employed in the art.

The present invention provides a method for preparing 4,4'-dihydroxy-[1,1'-biphenyl-3,3'-dicarboxylic acid] represented by Formula 1, including reacting the compound represented by Formula 2 with a base, as depicted in Reaction 1:

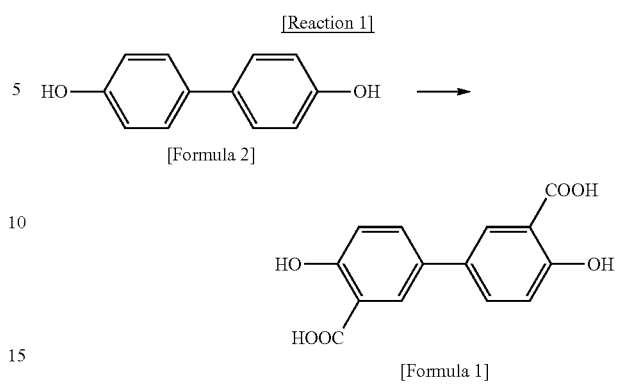

[Reaction 1]

[Formula 2]

[Formula 1]

Reaction 1 is carried out in a solvent represented by Formula 3:

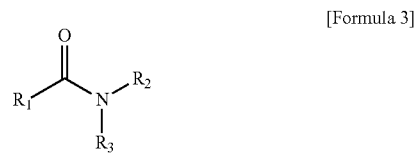

[Formula 3]

wherein $R_1$ is H or $-(CH_2)_n-CH_3$, $R_2$ is $-(CH_2)_m-CH_3$, $R_3$ is $-(CH_2)_p-CH_3$, and n, m, and p are each independently an integer from 0 to 20.

An amide-based solvent represented by Formula 3 is used in the synthesis of $H_4$dobpdc from 4,4'-biphenol([1,1'-biphenyl]-4,4'-diol) as a starting material, as depicted in Reaction 1. Since the use of the amide-based solvent improves the solubility of the reactant 4,4'-biphenol, a sludge of the product is formed to prevent the product from being hardened. In addition, the use of the amide-based solvent eliminates the need to separate the product using ether and enables acidification immediately after filtration because unreacted 4,4'-biphenol is dissolved in the solvent.

The amide-based solvent represented by Formula 3 is not limited as long as it can dissolve the reactant 4,4'-biphenol. The solvent represented by Formula 3 is preferably selected from N,N-dimethylformamide (DMF) represented by Formula 4, N,N-dimethylacetamide (DMAc) represented by Formula 5, N,N-diethylformamide (DEF) represented by Formula 6, and N,N-dibutylformamide represented by Formula 7.

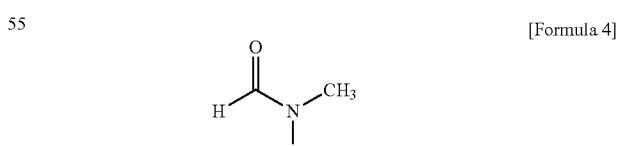

[Formula 4]

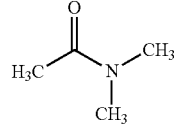

[Formula 5]

-continued

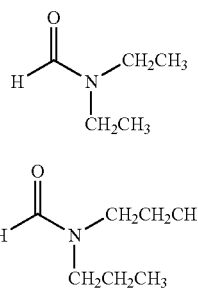

[Formula 6]

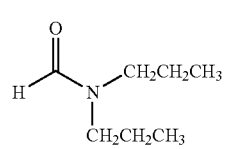

[Formula 7]

Dimethylformamide (DMF) is more preferred as the solvent.

The solvent is preferably used in an amount of 1 to 30 equivalents, more preferably 6 to 20 equivalents, per equivalent of the reactant 4,4'-biphenol.

Reaction 1 is carried out in the presence of a base. The base is preferably a carbonate compound selected from the group consisting of $K_2CO_3$, $Na_2CO_3$, $Li_2CO_3$, $KHCO_3$, $NaHCO_3$, $LiHCO_3$, and KOH. Particularly, the use of $K_2CO_3$, $Na_2CO_3$ or $Li_2CO_3$ as the base in the reaction eliminates the need to introduce carbon dioxide gas, which can be seen from the Examples section that follows. This prevents the internal pressure of the reactor from rising, and as a result, the reaction is allowed to proceed at a low temperature, achieving improved stability during the reaction.

The base is preferably used in an amount of 2 to 4 equivalents, more preferably 3 to 4 equivalents, per equivalent of the reactant 4,4'-biphenol.

Reaction 1 for synthesizing $H_4$dobpdc is preferably carried out at a temperature of 170 to 230° C. for at least 12 hours.

As described above, the use of the amide-based solvent and the carbonate base in Reaction 1 for synthesizing $H_4$dobpdc leads to significant improvements in reaction stability and yield. Particularly, the present invention establishes optimal conditions for synthesizing $H_4$dobpdc on a large scale. As can be seen from the Examples section that follows, $H_4$dobpdc can be synthesized on a large scale in a yield of 90% or higher when DMF as the amide-based solvent is used in an amount of 16.1 to 18.4 equivalents per equivalent of the reactant 4,4'-biphenol, $K_2CO_3$ as the carbonate base is used in an amount of 3 equivalents per equivalent of the reactant 4,4'-biphenol, and the reaction is carried out at a temperature of 200° C. for at least 72 hours.

MODE FOR CARRYING OUT THE INVENTION

EXAMPLES

The present invention will be explained in more detail with reference to the following examples. It will be evident to those skilled in the art that these examples are merely for illustrative purposes and are not to be construed as limiting the scope of the present invention. Therefore, the true scope of the present invention is defined by the appended claims and their equivalents.

Comparative Example 1. Synthesis of $H_4$dobpdc by the Prior Art Method (in 23 mL Reactor)

$H_4$dobpdc was synthesized in a 23 mL reactor by the method described in the literature (McDonald, T. M.; Lee, W. R.; Mason, J. A.; Weirs, B. M.; Hong, C. S.; Long, J. R. "Capture of Carbon Dioxide from Air and Flue Gas in the Alkylamine-Appended Metal-Organic Framework mmen-$Mg_2$(dobpdc)", J. Am. Chem. Soc. 2012, 134, 7056) (see FIG. 1). Specifically, 4,4'-biphenol and 3 equivalents of $KHCO_3$ as reactants and 1,2,4-trichlorobenzene as a solvent were used. The reactants were placed in a 23 mL steel reactor and dry ice was added thereto. The solvothermal reaction was carried out at 255° C. for 17 h. After completion of the reaction, the solid product was separated from the solvent by filtration, washed with ether, dissolved in distilled water, and acidified with hydrochloric acid. The resulting ligand was collected by filtration and recrystallized from acetone and distilled water. The yield of the ligand was found to be 40%.

Comparative Example 2. Synthesis of $H_4$dobpdc by the Prior Art Method (in 300 mL Reactor)

4,4'-Biphenol and 3 equivalents of $KHCO_3$ as reactants and 1,2,4-trichlorobenzene as a solvent were used. Before initiation of the reaction, ≥20 bar carbon dioxide gas was introduced into a 300 mL steel reactor and the solvothermal reaction was carried out with stirring at 250° C. for 72 h. After completion of the reaction, the solid product was separated from the remaining solvent by filtration and dissolved in ether to remove impurities. All remaining solvent and impurities were removed with ether, followed by filtration. The solid product thus obtained was dissolved in distilled water and stirred. The resulting solution was filtered and the filtrate was acidified with hydrochloric acid. The acidified product was washed several times with distilled water until neutrality and dried in an oven at ≥12 h to obtain a white ligand. The yield of the ligand was found to be 10%.

Example 1. Synthesis of $H_4$dobpdc by the Inventive Method (in 300 mL Reactor)

$H_4$dobpdc was synthesized by the method shown in FIG. 2. Specifically, 11.20 g of 4,4'-biphenol([1,1'-biphenyl]-4,4'-diol), 3 equivalents (24.93 g) of $K_2CO_3$, and 68 mL of N,N-dimethylformamide (DMF) were placed in a 300 mL steel reactor. The solvothermal reaction was carried out with stirring at 200° C. for 70 h. The product thus obtained was colored light pink and in the form of a sludge. The solvent DMF also turned red. The light pink product in the form of a sludge was separated from the DMF through a filter and acidified with hydrochloric acid. After completion of the acidification, the product was colored white. The acidified product was washed several times with distilled water until neutrality and dried in an oven at ≥12 h. The dried product was identified by nuclear magnetic resonance spectroscopy (FIG. 3). The yield was found to be ~95%.

Test Example 1. Determination of Whether the Product $H_4$dobpdc Became Sludge

The reaction products of Comparative Examples 1 and 2 were found to be hardened by the use of the reaction solvent trichlorobenzene (TCB) (see the left image of FIG. 4). The larger scale reaction had a greater influence on this hardening phenomenon. The hardened product impeded stirring during the reaction, and as a result, the reaction was not allowed to proceed smoothly, leading to a low yield of 10-40%. Separation with ether was also involved to remove the TCB.

In contrast, the use of the solvent DMF capable of readily dissolving the reactant 4,4'-biphenol in Example 1 enabled the synthesis of a larger amount of the product and formed a sludge of the product to prevent the product from being hardened (see the right image of FIG. 5). This sludge formation allowed the reaction to proceed perfectly even in the large-scale reactor, resulting in a yield as high as ≥95%. Since unreacted 4,4'-biphenol remained dissolved in the solvent, separation with ether was not necessary and acidification was enabled immediately after filtration.

Test Example 2. Determination of Internal Pressure and Reaction Temperature During $H_4$dobpdc Synthesis The use of the base $K_2CO_3$ in the reaction of Example 1 eliminated the need for the introduction of carbon dioxide gas, unlike the use of the base $KHCO_3$. Specifically, when the base $KHCO_3$ was used, 4,4'-biphenol was carboxylated by reaction with additionally introduced carbon dioxide, causing an increase in the internal pressure of the reactor (a maximum of ≥50 bar). For safety, a vent was installed to automatically release excess pressure when the pressure of the reactor reached 50 bar. When $K_2CO_3$ is used as a base, $CO_3^-$, $HCO_3^-$, and $H_2CO_3$ may exist as carbon dioxide sources necessary for carboxylation in the solvent. Meanwhile, when $KHCO_3$ is used as a base, $HCO_3^-$ and $H_2CO_3$ may exist as carbon dioxide sources necessary for carboxylation. $H_2CO_3$ is decomposed to carbon dioxide that is used for carboxylation. When $KHCO_3$ is used as a base, $H_2CO_3$ is completely decomposed rapidly to carbon dioxide, which is present in a gaseous state rather than is dissolved in the solvent. Thus, additional carbon dioxide needs to be dissolved in the solvent for the reaction. In contrast, when $K_2CO_3$ is used as a base, $HCO_3^-$ is gradually converted to $H_2CO_3$, which is also decomposed gradually to carbon dioxide. As a result, an appropriate amount of carbon dioxide may be dissolved in the solvent and the reaction may proceed without an additional supply of carbon dioxide.

For these reasons, the use of the base $K_2CO_3$ in Example 1 did not require the introduction of carbon dioxide, with the result that the maximum internal pressure was reduced to 43 bar, achieving good reaction stability. In addition, the use of the base $K_2CO_3$ instead of $KHCO_3$ was confirmed to lower the reaction temperature from 250° C. to 200° C. (FIG. 5).

Test Example 3. Determination of optimum conditions for $H_4$dobpdc synthesis

Experiments were conducted to investigate problems encountered in previously reported methods. Based on this investigation, factors affecting improvements in the yield of $H_4$dobpdc and optimum conditions for $H_4$dobpdc synthesis were determined in the following order.

(1) Measurement of Yields of $H_4$dobpdc Synthesized by Varying the Reaction Time in Comparative Example 1

$H_4$dobpdc was synthesized as described in Comparative Example 1 by varying the reaction time as shown in Table 1 and the yields of $H_4$dobpdc were measured.

TABLE 1

| I | Base | Solvent | Temperature | Carboxylation source | Reaction time | Yield |
|---|---|---|---|---|---|---|
| Literature report | $KHCO_3$ | TCB | 255° C. | Dry ice | 17 h | 40% |
| 1 | $KHCO_3$ | TCB | 250° C. | Dry ice | 6 h | X |
| 2 | $KHCO_3$ | TCB | 250° C. | Dry ice | 12 h | X |
| 3 | $KHCO_3$ | TCB | 250° C. | Dry ice | 24 h | 87% |
| 4 | $KHCO_3$ | TCB | 250° C. | Dry ice | 48 h | 89% |
| 5 | $KHCO_3$ | TCB | 250° C. | Dry ice | 72 h | 96% |

※ in 23 mL reactors

When the reaction time was 17 h as reported in the literature, the yield was as low as 40%, which is not suitable for the synthesis of $H_4$dobpdc on a large scale. As the reaction time increased, the yield increased. Particularly, when the reaction time was 72 h, the yield was improved to 96%. Hereinafter, $H_4$dobpdc was synthesized as described in Comparative Example 2 where the reaction time was set to 72 h.

(2) Measurement of Yields in Comparative Example 2

$H_4$dobpdc was synthesized as described in Comparative Example 2 where the optimum reaction time determined in (1) was applied, and the yields of $H_4$dobpdc were measured.

TABLE 2

| II | Base | Solvent | Temperature | Carboxylation source | Reaction time | Yield |
|---|---|---|---|---|---|---|
| 23 mL reactor | $KHCO_3$ | TCB | 250° C. | Dry ice | 72 h | 96% |
| 300 mL reactor | $KHCO_3$ | TCB | 250° C. | $CO_2$ gas (20 bar) | 72 h | 10-20% |

When the optimum reaction time determined (1) was applied to the 300 mL reactor, the use of TCB caused hardening of the product, with the result that the reaction was not allowed to proceed smoothly, resulting in a significantly low yield (10-20%). Considering this result, $H_4$dobpdc was synthesized using different solvents and its yields were measured.

(3) Measurement of Yields of $H_4$dobpdc when Different Types of Solvents were Used $H_4$dobpdc was synthesized using different reaction solvents, including TCB, MeOH, $H_2O$+MeOH, and DMF, as shown in Table 3.

TABLE 3

| III | Base | Solvent | Temperature | Carboxylation source | Reaction time | Yield |
|---|---|---|---|---|---|---|
| 1 | $KHCO_3$ | TCB | 250° C. | Dry ice | 72 h | 96% |
| 2 | $KHCO_3$ | MeOH | 130° C. | Dry ice | 72 h | X |
| 3 | $KHCO_3$ | $H_2O$ + MeOH | 130° C. | Dry ice | 72 h | X |
| 4 | $KHCO_3$ | DMF | 200° C. | Dry ice | 72 h | 67% |

※ In 23 mL reactors

The reaction temperature varied depending on the boiling point of the solvent used (boiling point: 210° C. for TCB and 150° C. for DMF). The use of DMF enabled the synthesis of $H_4$dobpdc in the form of a sludge. Considering this result, $H_4$dobpdc was synthesized using different bases and its yields were measured.

(4) Measurement of Yields of $H_4$dobpdc when Different Types of Bases were Used $H_4$dobpdc was synthesized using different types of bases, including $KHCO_3$, $NaHCO_3$, NaOME, KOH, and $K_2CO_3$, as shown in Table 4.

TABLE 4

| IV | Base | Solvent | Temperature | Carboxylation source | Reaction time | Yield |
|---|---|---|---|---|---|---|
| 1 | $KHCO_3$ | DMF | 200° C. | Dry ice | 72 h | 67% |
| 2 | $NaHCO_3$ | DMF | 200° C. | Dry ice | 72 h | X |
| 3 | NaOME | DMF | 200° C. | Dry ice | 72 h | X |
| 4 | KOH | DMF | 200° C. | Dry ice | 72 h | 51% |
| 5 | $K_2CO_3$ | DMF | 200° C. | Dry ice | 72 h | 95% |

※ In 23 mL reactors

The use of $K_2CO_3$ as a base enabled the synthesis of $H_4$dobpdc in a high yield of ≥95%. Considering this result, $H_4$dobpdc was synthesized using DMF as a solvent and $K_2CO_3$ as a base in 300 mL reactors and its yields were measured.

(5) Measurement of Yields of $H_4$dobpdc Synthesized in Reactors Having Different Volumes The reaction was carried out using TCB and DMF as solvents and $KHCO_3$ and $K_2CO_3$ as bases in 300 mL reactors, as shown in Table 5. The yields of $H_4$dobpdc were measured.

TABLE 5

| V | Base | Solvent | Temperature | Carboxylation source | Reaction time | Pressure | Yield |
|---|---|---|---|---|---|---|---|
| 1 | $KHCO_3$ | TCB | 250° C. | $CO_2$ gas (20 bar) | 72 h | 50 bar ↑ | 10-20% |
| 2 | $K_2CO_3$ | DMF | 200° C. | $CO_2$ gas (20 bar) | 70 h | 50 bar ↑ | 96% |

※ In 300 mL reactors

The use of DMF as a solvent and $K_2CO_3$ as a base formed a sludge of the product even in the large scale reactor to prevent the product from being hardened, with the result that the reaction was allowed to proceed smoothly to a yield of ≥96% and the reaction temperature was reduced. Considering this result, $H_4$dobpdc was synthesized with and without the introduction of carbon dioxide gas as a carboxylation source and its yields were measured.

(6) Measurement of Yields of $H_4$dobpdc Depending on Whether Carbon Dioxide Gas was Introduced The reaction was carried out using DMF as a solvent and $K_2CO_3$ as a base in 300 mL reactors, as shown in Table 6.

The yields of $H_4$dobpdc were measured depending on whether carbon dioxide gas as a carboxylation source was introduced.

TABLE 6

| VI | Base | Solvent | Temperature | Carboxylation source | Reaction time | Pressure | Yield |
|---|---|---|---|---|---|---|---|
| 1 | $K_2CO_3$ | DMF | 200° C. | $CO_2$ gas (20 bar) | 72 h | 50 bar ↑ | 96% |
| 2 | $K_2CO_3$ | DMF | 200° C. | X | 72 h | Max. 43 bar | 95% |

※ In 300 mL reactors

The use of DMF as a solvent and $K_2CO_3$ as a base enabled carboxylation of 4,4'-biphenol by $CO_2$ generated from $K_2CO_3$, with the result that $H_4$dobpdc was synthesized in a high yield of ≥95% irrespective of whether carbon dioxide gas was introduced. In addition, the internal pressure of the reactor was reduced to a maximum of 43 bar without the introduction of carbon dioxide gas. Hereinafter, the reaction was carried out in 300 mL reactors using different equivalents of different types of bases and different equivalents of different types of solvents at different reaction temperatures for different reaction times, and the yields of $H_4$dobpdc were measured.

(7) Measurement of Yields of $H_4$dobpdc when Different Types of Bases were Used $H_4$dobpdc was synthesized using DMF as a solvent and KOH, $KHCO_3$, and $K_2CO_3$ (3 equivalents each) as bases in 300 mL reactors, as shown in Table 7.

TABLE 7

| | 4,4'-biphenol | Base | DMF | $CO_2$ | Time | Temp | Yield |
|---|---|---|---|---|---|---|---|
| 1 | 11.20 g | KOH (10.12 g, 3 eq) | 70 mL | 20 bar | 72 h | 200° C. | 10.66 g (64.7%) |
| 2 | 11.20 g | $KHCO_3$ (18.06 g, 3 eq) | 70 mL | 20 bar | 72 h | 200° C. | 16.09 g (97.6%) |
| 3 | 11.20 g | $K_2CO_3$ (24.93 g, 3 eq) | 70 mL | X | 72 h | 200° C. | 15.01 g (91.0%) |

When DMF was used as a solvent and KOH, $KHCO_3$, and $K_2CO_3$ were used as bases, the yields were ≥60%. Particularly, the use of $K_2CO_3$ as a base did not require the introduction of carbon dioxide gas and led to a high yield (≥91%) of $H_4$dobpdc even at a low internal pressure of ≤43 bar.

(8) Measurement of Yields of $H_4$dobpdc when Different Equivalents of Base were Used $H_4$dobpdc was synthesized using DMF as a solvent and 1-4 equivalents of $K_2CO_3$ as a base in 300 mL reactors, as shown in Table 8.

TABLE 8

| | 4,4'-biphenol | Base | DMF | $CO_2$ | Time | Temp | Yield |
|---|---|---|---|---|---|---|---|
| 1 | 11.20 g | $K_2CO_3$ (8.3 g, 1 eq) | 70 mL | X | 72 h | 200° C. | — |
| 2 | 11.20 g | $K_2CO_3$ (16.62 g, 2 eq) | 70 mL | X | 72 h | 200° C. | 12.44 g (75.4%) |
| 3 | 11.20 g | $K_2CO_3$ (24.93 g, 3 eq) | 70 mL | X | 72 h | 200° C. | 15.01 g (91.0%) |
| 4 | 11.20 g | $K_2CO_3$ (33.24 g, 4 eq) | 70 mL | X | 72 h | 200° C. | 14.42 g (87.4%) |

When 2 to 4 equivalents of $K_2CO_3$ were used, the yields were ≥75%. Particularly, when 3 equivalents of $K_2CO_3$ was used, the yield of $H_4$dobpdc was as high as ≥91% even at an internal pressure as low as ≤43 bar.

(9) Measurement of Yields of $H_4$dobpdc Synthesized at Different Reaction Temperatures $H_4$dobpdc was synthesized using DMF as a solvent and 3 equivalents of $K_2CO_3$ as a base in 300 mL reactors at different reaction temperatures of 100 to 200° C., as shown in Table 9.

TABLE 9

| | 4,4'-biphenol | Base | DMF | $CO_2$ | Time | Temp | Yield |
|---|---|---|---|---|---|---|---|
| 1 | 11.20 g | $K_2CO_3$ (24.93 g, 3 eq) | 70 mL | X | 72 h | 100° C. | — |
| 2 | 11.20 g | $K_2CO_3$ (24.93 g, 3 eq) | 70 mL | X | 72 h | 150° C. | 2.66 g (16.1%) |
| 3 | 11.20 g | $K_2CO_3$ (24.93 g, 3 eq) | 70 mL | X | 72 h | 200° C. | 15.01 g (91.0%) |

The internal pressures of the reactors were reduced at very low temperatures of 100-150° C. but $H_4$dobpdc was not synthesized or synthesized in very low yield. In contrast, the yield of $H_4$dobpdc was high (≥91%) at a reaction temperature of 200° C. even when the internal pressure was reduced to ≤43 bar.

(10) Measurement of Yields of $H_4$dobpdc Synthesized for Different Reaction Times $H_4$dobpdc was synthesized using DMF as a solvent and 3 equivalents of $K_2CO_3$ as a base in 300 mL reactors for different reaction times of 12 to 96 h, as shown in Table 10.

TABLE 10

| | 4,4'-biphenol | Base | DMF | $CO_2$ | Time | Temp | Yield |
|---|---|---|---|---|---|---|---|
| 1 | 11.20 g | $K_2CO_3$ (24.93 g, 3 eq) | 70 mL | X | 12 h | 200° C. | 10.91 g (66.6%) |
| 2 | 11.20 g | $K_2CO_3$ (24.93 g, 3 eq) | 70 mL | X | 24 h | 200° C. | 12.08 g (73.2%) |
| 3 | 11.20 g | $K_2CO_3$ (24.93 g, 3 eq) | 70 mL | X | 48 h | 200° C. | 14.39 g (87.2%) |
| 4 | 11.20 g | $K_2CO_3$ (24.93 g, 3 eq) | 70 mL | X | 72 h | 200° C. | 15.01 g (91.0%) |
| 5 | 11.20 g | $K_2CO_3$ (24.93 g, 3 eq) | 70 mL | X | 96 h | 200° C. | 15.06 g (91.3%) |

When the reaction time was ≥12 h, the yield was ≥66%. Particularly, when the reaction time was ≥48 h, $H_4$dobpdc was synthesized in a high yield of ≥87%. When the reaction time was ≥72 h, $H_4$dobpdc was synthesized in a high yield of ≥91% at a low internal pressure of ≤43 bar.

(11) Measurement of Yields of $H_4$dobpdc when Different Types of Solvents were Used $H_4$dobpdc was synthesized using 3 equivalents of $K_2CO_3$ as a base and different types of solvents in 300 mL reactors, as shown in Table 11.

TABLE 11

| | Solvent | Boiling point | Solubility of starting | Product | Yield |
|---|---|---|---|---|---|
| 1 | $H_2O$ | 100° C. | Insoluble | Hardened | 1.18 g (67%) |
| 2 | Ethylene glycol | 197.6° C. | Insoluble | Hardened | — |
| 3 | Formamide | 210° C. | Insoluble | Hardened | — |
| 4 | N,N-Dimethylformamide | 153° C. | Soluble | Slurried | 1.64 g (93%) |
| 5 | NN-Dimethylacetamide | 165° C. | Soluble | Slurried | 1.67 g (95%) |
| 6 | N,N-Diethylformamide | 176-177° C. | Soluble | Slurried | 1.69 g (96%) |
| 7 | N,N-Dibutylformamide | 120° C. | Soluble | Slurried | 1.54 g (88%) |

The use of N,N-dimethylformamide (DMF), N,N-dimethylacetamide (DMAc), N,N-Diethylformamide (DEF), and N,N-dibutylformamide as solvents formed sludges of the products to prevent the products from being hardened, with the result that $H_4$dobpdc was synthesized in high yields of ≥90%.

(12) Measurement of Yields of $H_4$dobpdc when Different Equivalents of Solvent were Used $H_4$dobpdc was synthesized using 3 equivalents of $K_2CO_3$ as a base and 2.3-18.4 equivalents of DMF as a solvent in 300 mL reactors, as shown in Table 12.

TABLE 12

| | 4,4'-biphenol | $K_2CO_3$ | DMF | $CO_2$ | Time | Temp | Yield | Max Pressure |
|---|---|---|---|---|---|---|---|---|
| 1 | 11.20 g | 24.93 g (3 eq) | 10 mL (2.3 eq) | X | 72 h | 200° C. | 12.54 g (76%) | 21 bar |
| 2 | 11.20 g | 24.93 g (3 eq) | 20 mL (4.6 eq) | X | 72 h | 200° C. | 13.17 g (79%) | 22 bar |
| 3 | 11.20 g | 24.93 g (3 eq) | 30 mL (6.9 eq) | X | 72 h | 200° C. | 14.28 g (86%) | 36 bar |
| 4 | 11.20 g | 24.93 g (3 eq) | 40 mL (9.2 eq) | X | 72 h | 200° C. | 14.13 g (85%) | 42 bar |
| 5 | 11.20 g | 24.93 g (3 eq) | 50 mL (11.5 eq) | X | 72 h | 200° C. | 14.77 g (91%) | 42 bar |
| 6 | 11.20 g | 24.93 g (3 eq) | 60 mL (13.8 eq) | X | 72 h | 200° C. | 14.41 g (87%) | 40 bar |

TABLE 12-continued

| | 4,4'-biphenol | $K_2CO_3$ | DMF | $CO_2$ | Time | Temp | Yield | Max Pressure |
|---|---|---|---|---|---|---|---|---|
| 7 | 11.20 g | 24.93 g (3 eq) | 70 mL (16.1 eq) | X | 72 h | 200° C. | 15.01 g (91%) | 43 bar |
| 8 | 11.20 g | 24.93 g (3 eq) | 80 mL (18.4 eq) | X | 72 h | 200° C. | 15.32 g (92%) | 43 bar |

When 2.3-18.4 equivalents of DMF were used, the yields were ≥76%. Particularly, H$_4$dobpdc was synthesized in high yields of ≥85% when ≥6.9 equivalents of DMF were used. In addition, H$_4$dobpdc was synthesized in high yields of ≥91% at low internal pressures of ≤43 bar when ≥16.1 equivalents of DMF were used.

Although the particulars of the present disclosure have been described in detail, it will be obvious to those skilled in the art that such particulars are merely preferred embodiments and are not intended to limit the scope of the present invention. Therefore, the true scope of the present invention is defined by the appended claims and their equivalents.

INDUSTRIAL APPLICABILITY

According to the present invention, H$_4$dobpdc can be synthesized in a greatly improved yield through a relatively simple process. Therefore, the present invention is useful in the development of carbon dioxide adsorbents based on metal-organic frameworks where mass production of H$_4$dobpdc is needed.

The invention claimed is:

1. A method for preparing 4,4'-dihydroxy-[1,1'-biphenyl-3,3'-dicarboxylic acid] represented by Formula 1, comprising reacting the compound represented by Formula 2 with a base, as depicted in Reaction 1:

[Reaction 1]

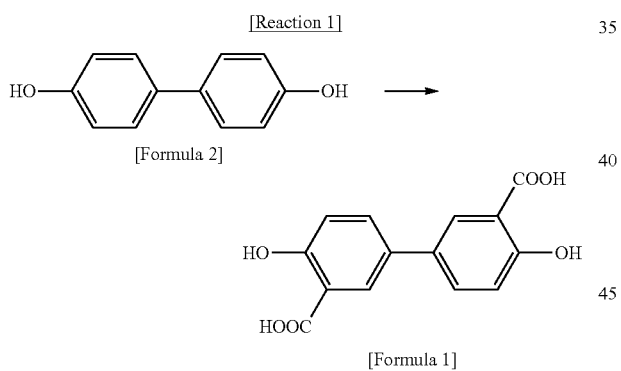

[Formula 2]

[Formula 1]

wherein Reaction 1 is carried out in a solvent represented by Formula 3:

[Formula 3]

wherein R$_1$ is H or —(CH$_2$)$_n$—CH$_3$, R$_2$ is —(CH$_2$)$_m$—CH$_3$, R$_3$ is —(CH$_2$)$_p$—CH$_3$, and n, m, and p are each independently an integer from 0 to 20, wherein the base is selected from the group consisting of K$_2$CO$_3$, Na$_2$CO$_3$, and Li$_2$CO$_3$.

2. The method according to claim 1, wherein the solvent represented by Formula 3 is selected from the group consisting of the compounds represented by Formulae 4 to 7:

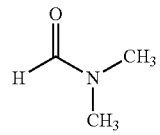

[Formula 4]

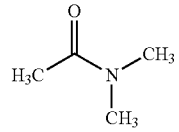

[Formula 5]

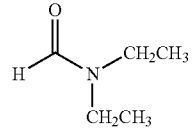

[Formula 6]

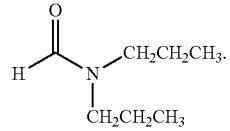

[Formula 7]

3. The method according to claim 1, wherein the base is used in an amount of 2 to 4 equivalents per equivalent of the compound represented by Formula 2.

4. The method according to claim 1, wherein the solvent represented by Formula 3 is used in an amount of 1 to 30 equivalents per equivalent of the compound represented by Formula 2.

5. The method according to claim 1, wherein Reaction 1 is carried out at a temperature of 170 to 230° C.

6. The method according to claim 1, wherein Reaction 1 is carried out for at least 12 hours.

* * * * *